United States Patent [19]
Rakli et al.

[11] 4,278,654
[45] Jul. 14, 1981

[54] PROCESS FOR THE PREPARATION OF A STERILE INJECTABLE PHYSIOLOGICALLY ACCEPTABLE SOLUTION OF AN X-RAY CONTRAST AGENT AND SOLUTIONS OF THE X-RAY CONTRAST AGENT AND A BUFFER

[75] Inventors: Fridtjov B. Rakli; Michael J. Kelly, both of Oslo, Norway

[73] Assignee: Nyegaard & Co. A/S, Oslo, Norway

[21] Appl. No.: 54,440

[22] Filed: Jul. 3, 1979

[30] Foreign Application Priority Data

Jul. 4, 1978 [GB] United Kingdom ............... 28764/78

[51] Int. Cl.$^3$ ............................................. A61K 49/04
[52] U.S. Cl. ......................................................... 424/5
[58] Field of Search ........................................... 424/5

[56] References Cited

U.S. PATENT DOCUMENTS

| 3,733,397 | 5/1973 | Bjork et al. | 424/5 |
| 3,910,989 | 10/1975 | Felder et al. | 424/5 |
| 4,132,731 | 1/1979 | Klieger et al. | 424/5 |

FOREIGN PATENT DOCUMENTS

| 229151 | 10/1958 | Australia | 424/5 |
| 3758 | 10/1963 | France | 424/5 |
| 1023495 | 3/1966 | United Kingdom | 424/5 |
| 1069437 | 5/1967 | United Kingdom | 424/5 |
| 1542677 | 3/1976 | United Kingdom | 424/5 |
| 1450524 | 9/1976 | United Kingdom | 424/5 |
| 1514920 | 6/1979 | United Kingdom | 424/5 |

OTHER PUBLICATIONS

The Extra Pharmacopoeia, 26th ed., pp. 461, 466 and 467.

Primary Examiner—Frederick E. Waddell
Attorney, Agent, or Firm—Bacon & Thomas

[57] ABSTRACT

Sterile, injectable, physiologically acceptable solutions of an X-ray contrast agent are prepared by autoclaving a solution of a m-carboxamido-o-iodo-N-($\beta$-hydroxyalkyl)aniline X-ray contrast agent in the presence of a physiologically acceptable buffer system the pH of which decreases with increasing temperature.

The presence of a temperature dependent buffer, preferably an amine, enables X-ray contrast agents to be sterilized by autoclaving without significant decomposition.

Examples of the autoclaving processes are given and solutions for autoclaving containing a m-carboxamido-o-iodo-N-($\beta$-hydroxyalkyl)aniline X-ray contrast agent and a physiologically acceptable buffer system the pH of which decreases with increasing temperature are described and claimed.

10 Claims, No Drawings

PROCESS FOR THE PREPARATION OF A STERILE INJECTABLE PHYSIOLOGICALLY ACCEPTABLE SOLUTION OF AN X-RAY CONTRAST AGENT AND SOLUTIONS OF THE X-RAY CONTRAST AGENT AND A BUFFER

The present invention relates to the preparation of sterile, injectable physiologically acceptable solutions of X-ray contrast agents by autoclaving and more particularly to the preparation of such solutions at a physiologically acceptable pH which contain substances unstable when autoclaved at physiologically acceptable pH levels.

A difficulty encountered with certain solutions for administration e.g. by injection to human beings is that although the properties of the active compounds are very beneficial it is difficult, if not impossible, to sterilize the solutions by autoclaving at a physiologically acceptable pH e.g. in the range 6.8 to 8.0, with decomposition taking place or without the sterilization process effecting a change which renders the compound unsuitable for use. The term "solution" as used herein refers to aqueous or predominantly aqueous solutions. The extent of this decomposition can often be substantially reduced by autoclaving at a lower pH e.g. pH 5, but a solution at this pH is physiologically unacceptable when injected in substantial quantities. Various methods may be employed to overcome the disadvantage of low pH, for example neutralization after autoclaving or at the time of use, but such ad hoc methods have generally proved unsatisfactory.

The use of a buffer in the formulation of the solution to be autoclaved has been considered and has, hitherto, proved unsuccessful. Indeed it has been found that in many cases acid is produced by the decomposition of the active product and, in reducing the pH, eventually stabilises the system; consequently when a buffer is included in the formulation of such a solution in order to maintain its pH constant at pH 7.0 to 7.5 even more decomposition takes place during autoclaving than when the pH is allowed to fall. Thus, for example, conventional buffers such as alkali metal phosphates, citrates, lactates, carbonates and carboxylates have all been found to be unsuccessful in stabilising such solutions against autoclaving.

The present invention is directed to the autoclaving of X-ray contrast agents which are required for injection in solution at a physiologically acceptable pH which, at autoclaving temperatures, are unstable at said physiologically acceptable pH but stable at a lower pH. The present invention is based on the discovery that such a solution at a physiologically acceptable pH may successfully be autoclaved without significant decomposition and on cooling to ambient temperature yield a sterile solution at a physiologically acceptable pH, if autoclaving is effected in the presence of a buffer system the pH of which decreases with increasing temperature. In such a system, the pH of the solution is reduced at the high temperature of autoclaving but returns to a physiological pH on cooling.

The invention also extends to aqueous solutions containing said unstable X-ray contrast agents together with a buffer system the pH of which decreases with increasing temperature.

It will be appreciated that while solutions having a non-physiologically acceptable pH may be injected intravenously in small doses (although this is preferably avoided if possible) it is obviously very important to avoid the intravenous injection of large quantities of a solution which does not have a physiologically acceptable pH. The present invention is thus of particular importance because solutions of X-ray contrast agents are normally administered in relatively large quantities.

The majority of X-ray contrast agents are in general stable; they may be sterilized by autoclaving without change of pH or liberation of iodide and may be stored subsequently without deterioration. It has been found that the presence of hydroxyalkyl groups, especially alkyl groups with a hydroxy substituent on a carbon atom $\beta$ to an acylamido nitrogen, in such X-ray contrast agents is particularly advantageous in terms of increased solubility and reduced toxicity. Unfortunately the presence of such groups has been found in certain cases to result in instability at neutral pH and high temperature so that it is difficult to sterilize solutions of such compounds as formulated by conventional pharmaceutical procedures, by autoclaving.

In particular, it is believed that certain X-ray contrast agents containing the m-carboxamido-o-indo-N-($\beta$-hydroxyalkyl)aniline moiety cyclize during autoclaving at physiologically acceptable pHs or higher pHs according to the general reaction sequence:

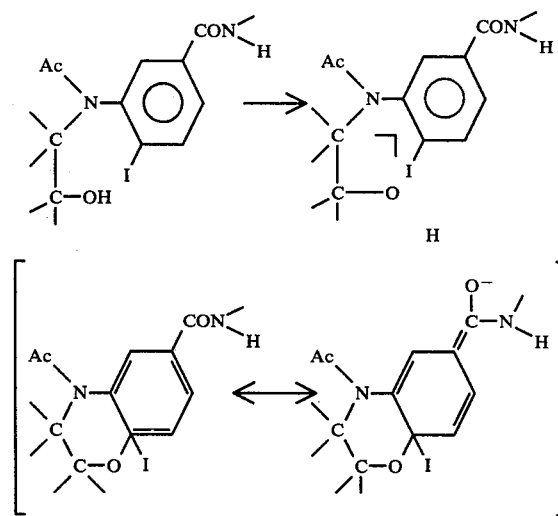

(where Ac represents an acyl group) followed by liberation of iodide and acetate to form a compound of the type

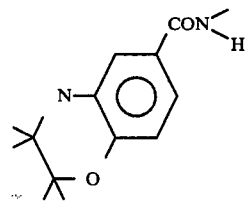

with concomitant formation of $H_3O^\oplus$ and hence reduction of pH. Thus the process of the present invention is especially applicable to such compounds in which the nitrogen atom carries a group capable of intramolecular cyclization to form a stabilized intermediate of the above type.

Thus according to one feature of the present invention there is provided a process for the preparation of a sterile, injectable, physiologically acceptable solution of an X-ray contrast agent which comprises autoclaving a solution of a m-carboxamido-o-iodo-N-(β-hydroxyalkyl)-aniline X-ray contrast agent in the presence of a physiologically acceptable buffer system the pH of which decreases with increasing temperature. X-ray contrast agents which are of particular interest for use in the process of the present invention, are non-ionic X-ray contrast agents of the formula:

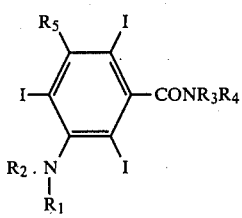

wherein $R_1$ represents either (a) the group

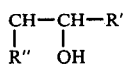

in which R' and R", which may be the same or different, each represents a hydrogen atom or an alkyl group with 1 to 4 carbon atoms which may, if desired, carry one or more —OH groups, or (b) a sugar residue having a β—OH group at the 2-,3- or 4- position, the said —OH group being bonded to the carbon atom β to the acetamido nitrogen atom; $R_2$ represents an acyl group; $R_3$ and $R_4$, which may be the same or different, each represent a hydrogen atom or an alkyl, hydroxyalkyl or acyloxyalkyl group or a sugar residue; and $R_5$ represents a hydrogen atom or the group —$CONR_3''R_4''$, $Ac'NR^6$ or —$CH_2NAc'$ $R^6$ (in which $R_3''$ and $R_4''$, which may be the same or different, each represents a hydrogen atom or an alkyl, hydroxyalkyl or acyloxyalkyl group or a sugar residue and $R^6$ represents a hydrogen atom or an alkyl, hydroxyalkyl, acyloxyalkyl or acyl group).

Thus for example $R_1$ may represent a —$CH_2CH_2OH$, —$CH_2CHOHCH_2OH$ or $(CH_2OH)_2CH$— group.

$R_2$ is preferably a lower aliphatic acyl group (advantageously having 1–6 carbon atoms) and may, for example, be derived from a carboxylic or sulphonic acid.

Where $R_3,R_4,R_3'',R_4''$ and/or $R_6$ represents a hydroxylalkyl group this group may carry a single hydroxy group, as in the β-hydroxyethyl group, or more than one hydroxy group as in the dihydroxypropyl or tris-(hydroxymethyl)-methyl group or in the polyhydroxyalkyl portion of hexosamines, pentosamines, and sugar amino-alcohols such as glucosamine or glucamines e.g. N-methyl glucamine, 1-glucamine or 2-glucamine. Other non-ionic substituents may also be present, for example the aldehyde group, as present in glucosamine, or one or more acyloxy groups.

The alkyl, hydroxyalkyl and aliphatic acyl groups which are present preferably contain 1–6 carbon atoms. Preferred alkyl groups thus include methyl, ethyl, propyl, butyl and hexyl groups; the methyl group is preferred and an N-methyl substituent often enhances water solubility.

The acyl group $R^2$ or Ac may for example, be derived from a carboxylic acid or a sulphonic acid.

Preferred acyl groups derived from carboxylic acids, which may be O-attached or N-attached include $C_{2-4}$ alkanoyl e.g. acetyl, propionyl and butyryl groups, the acetyl group being most preferred. The acyl groups may if desired, carry one or more hydroxy substituents. Preferred acyl groups derived from sulphonic acids include alkane sulphonyl groups such as the methane sulphonyl group.

The alkyl, hydroxyalkyl and acyl groups which are present may additionally carry a further non-ionic iodinated hydrocarbon grouping which may carry additional amide groups and, thus, for example, an alkylene, hydroxyalkylene or a diacyl grouping derived from a dibasic acid may be N-bonded at either end to iodinated hydrocarbons carrying amide groupings.

The concentration of radiopaque in solution will normally be for example in the range 100 to 450 mg I per ml.

It is important to ensure that the temperature dependent buffer used has sufficient buffer capacity; in general the pKa of the buffer at room temperature should be near to or in the physiological range 6.8 to 7.6 since the buffer capacity falls off at pH values substantially higher or lower than the pKa. If the buffer capacity is high, less ionic material is required and the osmolality of the solution may thus be kept as low as possible. pKa values at 15° C. of less than or equal to 9.5 are thus, in general, preferred. In this connection it should be emphasised that it is the considered opinion among some specialists that certain toxic side effects are due, at least in part, to the osmotic imbalance created by injecting very large concentrations of dissolved material into the body fluids.

The osmolality of a solution of a chemical compound is normally approximately directly proportional to the sum of the concentrations of the different molecular or ionic species which are present. A water-soluble salt, for example the sodium salt of an iodinated acid, will normally be almost completely ionised and the osmolality will be proportional to the concentration of both the anion and the cation. The total concentration of ionic species will thus be approximately twice that of the salt considered as a single unionised species. In contrast, the osmolality of a non-ionic compound e.g. of the type described in our British Pat. No. 1,321,591, that is a compound which is substantially unionised in aqueous solution, is expected to be approximately proportional simply to the molarity of the compound present, that is approximately half the value for an analogous ionic compound having two ionic species. It is thus important to ensure that the osmolality of the solution of the temperature dependent buffer and the compound to be autoclaved, for example the X-ray contrast agent, is as low as possible.

In general, the ionic strength of the buffer should preferably not exceed about 15%, especially 10% of the molar concentration of the substrate if the osmolality or toxicity of the solution is not to be significantly impaired. Some compounds which are used at lower molar concentration for example the bis X-ray contrast agents referred to above, may be capable of tolerating a higher buffer concentration expressed as a percentage of its molar concentration. In general, the concentration of the buffer in the solution is thus preferably not greater than 50 m.molar, more preferably in the range 5 to 25 m.molar.

As will be appreciated a solution of a compound to be autoclaved according to the present invention and a temperature dependent buffer will have a physiologically acceptable pH at room temperature (15° C.) e.g. 6.8 to 8.0. As the temperature of the solution is raised in the autoclave the pH of the solution will decrease. Thus if the solution has a pH of 7.4 at room temperature this pH may drop, for example by about 2.5 pH units to a pH of 4.9 at 120° C. On allowing the solution to cool, the pH will increase, but may not necessarily return to as high a pH at room temperature as the solution possessed prior to autoclaving. Thus for example a solution which possesses a pH of 7.6 at room temperature prior to autoclaving may possess a pH of 7.4 at room temperature after autoclaving. This is generally due to a very small amount of acid generating decomposition which is nevertheless acceptable physiologically.

Thus, for example, the pH of the solution at room temperature prior to autoclaving is preferably 7.0 to 7.6 falling preferably to 3.5 to 5.5 especially about 4.5, during autoclaving and subsequently returning preferably to a pH of 7.0 to 7.6 at room temperature after autoclaving. The change of pH of the solution at room temperature before and after autoclaving may, for example, be <0.2 of a pH unit in respect of radiopaques autoclaved in accordance with the invention.

The autoclaving temperature employed for effecting sterilization is correlated with time. Thus, if a relatively low autoclaving temperature is employed, e.g. 110° C., the autoclaving is, in general, conducted for a longer period of time. One advantageous feature of the present invention is that sterilization by autoclaving may be conducted at higher temperatures and for a shorter time than hitherto conventional without decomposing the product to be sterilized. In such processes the pH of the solution at the higher autoclaving temperature will be even lower due to the greater pH reduction of the buffer, for example, about 0.5 of a pH unit lower at 140° C. and about 1.0 pH unit lower at 160° C. as compared with the pH at 120° C.

Temperature dependent buffers which may be employed in the solutions to be autoclaved include, in particular, ammonia and physiologically acceptable water soluble amines having a pKa at 15° C. $\leq 9.5$. In general, these will be of the formula $$NR^1R^2R^3 \quad (II)$$

wherein $R^1, R^2$ and $R^3$, which may be the same or different, each represents a hydrogen atom, a sugar residue, an alkyl group with 1 to 6 carbon atoms which may carry one or more hydroxy, mercapto, carboxyl, carboxamido, imidazolyl, indolyl or hydroxy substituted phenyl groups, alkylthio groups with 1 to 6 carbon atoms and/or groups of the formula: $-NR^4R^5$ (in which $R^4$ and $R^5$, which may be the same or different, each represents a hydrogen atom, a carboxamido or

group or an alkyl group with 1 to 6 carbon atoms); or any two of $R^1 R^2$ and $R^3$ may, together with the intervening nitrogen atom, represent a pyrrolidine or piperidine ring which may carry hydroxy, carboxyl or carboxamido groups.

Thus, for example, the physiologically acceptable, water soluble amines which may be employed as temperature dependent buffers include amino alcohols and amino sugars. Preferred amines for use in the process of the present invention include "Tris" [tris(hydroxymethyl)methylamine], AMPD [2-amino-2-methylpropane-1,3-diol], diethanolamine, meglumine, triethanolamine and ammonia. Especially preferred amines for use in the process of the present invention are "Tris" and meglumine in view of their advantageous physiological acceptability. "Bis-Tris" [N,N-bis(2-hydroxyethyl)-tris(-hydroxymethyl)-methylamine] is an especially preferred amine for use in the process of the present invention in view of its advantageous pKa value of 6.5 at 25° C.

In formulating the solutions for autoclaving it is generally preferred to ensure that no anions such as carboxylates, phosphates and citrates, especially the anions of weak acids having a pKa>2, are present.

The solutions for autoclaving will generally possess conventional adjuvents such as chelating agents e.g. ethylenediamine tetraacetate.

According to a further feature of the present invention there is provided a solution of a m-carboxamido-o-iodo-N-(β-hydroxyalkyl)-aniline X-ray contrast agent and a physiologically acceptable buffer system the pH of which decreases with increasing temperature.

The buffer is preferably an amine buffer of formula II as hereinbefore defined. The amine buffer is conveniently the sole buffer present in the system.

The solution preferably comprises meglumine or tris(hydroxymethyl) methylamine as the amine buffer.

The concentration of the buffer in the solution is advantageously no greater than 50 m. molar especially in the range 5 to 25 m. molar.

The m-carboxamido-o-iodo-N-(β-hydroxyalkyl)aniline X-ray contrast agent is preferably of formula I as hereinbefore defined especially 5-(N-2,3-dihydroxypropylacetamido)-2,4,6-triiodo-N,N-bis(2,3-dihydroxypropyl)isophthalamide.

The following Examples 1–7 illustrate the invention:

COMPARATIVE EXAMPLE

The stability of various radiopaques to autoclaving in the absence of a buffer is shown in the following Table I in which both the pH and the iodide ion concentration is noted before and after autoclaving. Solutions were prepared using conventional adjuvants, in particular 0.2 mg/ml of ethylenediamine tetraacetate; the concentration of X-ray contrast agent was 300 mg I/ml:

Compound I=5,-N-2-hydroxyethylacetamido-2,4,6-triiodo-N,N'-bis(2,3-dihydroxypropyl)isophthalamide;

Compound II=5-N-(2,3-dihydroxypropyl)acetamido-2,4,6-triiodo-N,N'-bis(2-hydroxyethyl)isophthalamide;

Compound III=3,5-bis-N,N'-(2,3-dihydroxypropyl)acetamido-2,4,6-triiodo-N-(2-hydroxyethyl)-benzamide;

Compound IV=5-N-(2-hydroxyethyl)acetamido-2,4,6-triiodo-N,N'-dimethyl-N,N'-bis-(2,3-dihydroxypropyl)isophthalamide;

Compound V=5-(N-2,3-dihydroxypropylacetamido)-2,4,6-triiodo-N,N'-bis(2,3-dihydroxypropyl)-isophthalamide.

TABLE I

| | Compound/buffer | pH before | after | change | $I^{\ominus}\mu g/ml$ before | after | change |
|---|---|---|---|---|---|---|---|
| A | Compound I/8mM phosphate | 7.39 | 7.04 | −0.35 | 4 | 130 | +126 |
| B | Compound I/5mM bicarbonate | 7.57 | 6.75 | −1.0 | 4 | 108 | +104 |
| C | Compound II/10mM phosphate | 7.53 | 6.89 | −0.64 | 3 | 310 | +307 |
| D | Compound II/10mM $HCO_3^-$ | 7.51 | 6.81 | −0.70 | 3 | 266 | +263 |

Examples

Compounds previously found to be unstable at autoclaving temperatures were subjected to autoclaving in the presence of certain temperature dependent buffers

TABLE II.

| | | Effect of various buffers on autoclaving stability | | | |
|---|---|---|---|---|---|
| No. | Compound | Buffer | pH before | pH after | $I^-$ before | $I^-$ after |
| 1 | Compound I | 10 mM TRIS | 7.34 | 7.34 | 4 | 8 |
| 2 | | 20 mM meglumine | 7.65 | 7.53 | 2 | 10 |
| 3 | Compound II | 10 mM TRIS | 7.45 | 7.41 | 3 | 13 |
| 4 | | 10 mM meglumine | 7.42 | 7.13 | 3 | 15 |
| 5 | Compound III | 10 mM TRIS | 7.50 | 7.35 | ≦8 | 23 |
| 6 | Compound IV | 10 mM TRIS | 7.49 | 7.60 | 14 | 14 |
| 7 | Compound V | 10 mM TRIS | 7.53 | 7.43 | 5 | 11 |

As will be seen from the above results the compounds could be sterilized by autoclaving without substantial change of pH and iodide ion concentration.

We claim:

1. A process for the preparation of a buffered sterile, injectable, physiologically acceptable solution of an X-ray contrast agent which comprises autoclaving a solution of a m-carboxamido-o-iodo-N-(β-hydroxyalkyl)-aniline X-ray contrast agent in the presence of a physiologically acceptable buffer which is selected from the group consisting of ammonia and a water soluble amine having a pKa of ≦9.5 at 15° C. and which causes a decrease of the pH of the buffered solution with increasing temperature.

2. A process as claimed in claim 1 wherein the m-carboxamido-o-iodo-N-(β-hydroxyalkyl)aniline X-ray contrast agent is of the formula:

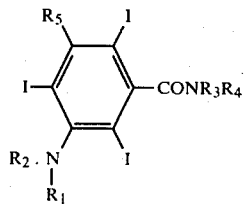 (I)

wherein $R_1$ represents either (a) the group

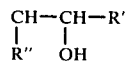

in which R' and R", which may be the same or different, each represents a hydrogen atom or an alkyl group with 1 to 4 carbon atoms which may carry one or more —OH groups, or (b) a sugar residue having a β-OH group in β-position to the nitrogen atom to which the sugar residue is attached, said β-position being the 2-, 3- or 4-position within the sugar residue; $R_2$ represents an alkylcarbonyl or alkylsulphonyl group containing 1 to 6 carbon atoms; $R_3$ and $R_4$, which may be the same or different, each represent hydrogen, $C_1$–$C_6$ alkyl, $C_1$–$C_6$ hydroxyalkyl or an acyloxy $C_1$–$C_6$ alkyl group wherein the acyl group is an alkylcarbonyl or alkylsulphonyl group containing 1–6 carbon atoms or a sugar residue; and $R_5$ represents a hydrogen atom or the group —$CONR_3''R_4''$, $Ac'NR^6$ or —$CH_2NAc'$ $R^6$ in which $R_3''$ and $R_4''$, which may be the same or different, each represents hydrogen, $C_1$–$C_6$ alkyl, $C_1$–$C_6$ hydroxyalkyl or an acyloxy $C_1$–$C_6$ alkyl group wherein the acyl group is an alkylcarbonyl or alkylsulphonyl group containing 1 to 6 carbon atoms or a sugar residue, Ac' is an alkylcarbonyl or alkylsulphonyl group containing 1 to 6 carbon atoms, and $R^6$ represents hydrogen, $C_1$–$C_6$ alkyl, $C_1$–$C_6$ hydroxyalkyl, or an acyloxy $C_1$–$C_6$ alkyl or acyl group wherein the acyl group is an alkylcarbonyl or alkylsulphonyl group containing 1–6 carbon atoms.

3. A process as claimed in claim 1 wherein the concentration of X-ray contrast agent in the solution to be autoclaved is 100 to 450 mg I per ml.

4. A process as claimed in claim 1 wherein the concentration of the buffer in the solution is no greater than 50 m.molar.

5. A process as claimed in claim 4 wherein the concentration of the buffer in the solution is in the range 5 to 25 m.molar.

6. A process as claimed in claim 1 wherein the buffer is a physiologically acceptable water soluble amine of the formula:

$$NR^1R^2R^3 \quad (II)$$

wherein $R^1$, $R^2$ and $R^3$, which may be the same or different, each represents a hydrogen atom, a sugar residue, an alkyl group with 1 to 6 carbon atoms which may carry one or more hydroxy, mercapto, carboxyl, carboxamido, imidazolyl, indolyl or hydroxy substituted phenyl groups, alkylthio groups with 1 to 6 carbon atoms and/or groups of the formula: —$NR^4R^5$ (in which $R^4$ and $R^5$, which may be the same or different, each represents a hydrogen atom, a carboxamido or

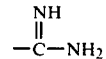

group or an alkyl group with 1 to 6 carbon atoms); or any two of $R^1$, $R^2$ and $R^3$ may, together with the intervening nitrogen atom, represent a pyrrolidine or piperidine ring which may carry hydroxy, carboxyl or carboxamido groups.

7. A process as claimed in claim 6 wherein the water soluble amine comprises tris-(hydroxymethyl)methylamine, meglumine or N,N-bis(2-hydroxyethyl)-tris(hydroxymethyl)-methylamine.

8. A process as claimed in claim 1 wherein the solution to be autoclaved contains a chelating agent.

9. A process as claimed in claim 8 wherein the chelating agent comprises ethylenediamine tetraacetate.

10. A process as claimed in claim 1 or claim 2 wherein the m-carboxamido-o-iodo-N-(β-hydroxyalkyl)aniline X-ray contrast agent is 5-(N-2,3-dihydroxypropylacetamido)-2,4,6-triiodo-N,N'-bis(2,3-dihydroxypropyl)isophthalamide.

* * * * *